US009016671B1

(12) United States Patent
McCaskey

(10) Patent No.: US 9,016,671 B1
(45) Date of Patent: Apr. 28, 2015

(54) COAXIAL NEEDLE ATOMIZING SYSTEM

(71) Applicant: U.S. Army Research Development and Engineering Command, APG, MD (US)

(72) Inventor: David A. McCaskey, Parkville, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 225 days.

(21) Appl. No.: 13/795,797

(22) Filed: Mar. 12, 2013

(51) Int. Cl.
*B01F 3/04* (2006.01)
*A61M 11/00* (2006.01)
*B05B 17/00* (2006.01)

(52) U.S. Cl.
CPC ............ *B05B 17/00* (2013.01); *B01F 3/04063* (2013.01); *B01F 3/04* (2013.01); *B01F 3/04021* (2013.01); *A61M 11/007* (2014.02)

(58) Field of Classification Search
CPC .... B01F 3/04; B01F 3/04021; B01F 3/04063; A61M 11/00; A61M 11/007
USPC ........ 261/76, 78.2; 128/200.14; 239/369, 398
See application file for complete search history.

(56) References Cited

U.S. PATENT DOCUMENTS 8,882,085 B1 * 11/2014 Horsmon et al. ............ 261/78.2

* cited by examiner

*Primary Examiner* — Robert A Hopkins
(74) *Attorney, Agent, or Firm* — Ulysses J. Biffoni

(57) ABSTRACT

An atomizing system tar generating an aerosol for inhalation research is disclosed. The atomizing system, in one embodiment, is capable of functioning efficiently at ultra-low liquid and low gas feed rates through the use of a 32 gauge feed line. This feed line reduces dead space in the atomizing system as well as the amount of highly toxic and/or expensive fluid needed to perform the research. An aerosol is generated in a consistent and repeatable manner by injecting fluid at a teed rate of 0.2-20 μl/min into a gas stream from a compressed gas source at a pressure of 30-60 psi. An adapter is used to connect a syringe containing the fluid to be tested to the 32 gauge feed line.

2 Claims, 2 Drawing Sheets

FIG. 1

COAXIAL NEEDLE ATOMIZING SYSTEM

GOVERNMENT INTEREST

The invention described herein may he manufactured, used and licensed by or for the U.S. Government.

FIELD OF THE INVENTION

The present invention relates generally to generating aerosols at very low liquid and gas feed rates.

BACKGROUND

Inhalation research often requires working with highly toxic and/or expensive compounds. These compounds are typically in a liquid form and must be converted to an aerosol in a respirable range for the purposes of conducting experiments. It is imperative that the aerosols have a consistent particle size and concentration and that they are reproducible during numerous experiments over a period of time.

An additional requirement of inhalation research is that the compounds must be used undiluted (neat) to eliminate an effect caused by solvents. Since the compounds are often expensive and/or highly toxic, it is essential to use the minimal amount necessary for safety and cost effectiveness. Further research with compounds that are often highly toxic requires the use of a glove box, or double containment device, which imposes size constraints on the size of the equipment. In particular, small volume chambers for the exposures are required and therefore, a low gas flow generator is needed.

Prior art syringe drives and syringes used with conventional fittings and feed lines in an annular atomizer tend to experience pulsing, spitting and sputtering, especially at the ultra low flow rates. This is due to the surface tension of the dispensed fluid breaking at the point of generation in normal inner diameter feed lines. Prior art systems also experience an oscillation in output due to the earn action of syringe drive feed systems.

Thus, a need exists for a micro atomizing system capable of functioning efficiently at ultra-low liquid and low gas feed rates.

SUMMARY

The invention in one embodiment encompasses an atomizing system with reduced dead space provided by a very small diameter fluid compound feed line and a containment system for using the atomizing system to perform inhalation research. In one embodiment, the atomizing system includes:

a tee fitting having a main bore and as secondary bore perpendicular to the main bore, the secondary bore coupled to as compressed gas source at as pressure of approximately 30-60 psi;

a tube extending through the main bore of the tee fitting, wherein a first end of the tube adjacent to a first end of the main bore of the tee fitting is attached to a syringe and is capable of receiving a fluid compound from the syringe at a feed rate of 0.2-20 µl/min; and a needle attached to a second end of the main bore of the tee fitting, the needle receiving compressed gas from the secondary bore and the main bore of the tee fitting;

wherein the tube extends through the tee fitting and the needle so that a second end of the tube extends slightly beyond the needle and fluid is injected from the end of the tube into the compressed gas flow from the annular opening between the tube and the needle.

In another embodiment, the atomizing system includes a tee fitting haying a main bore and a secondary bore perpendicular to the main bore, the secondary bore coupled to a compressed gas source;

a 32 gauge tube extending through the main bore of the tee fitting, wherein a first end of the 32 gauge tube adjacent to a first end of the main bore of the tee fitting is attached to a syringe and is capable of receiving a fluid compound from the syringe; and a 22 gauge needle attached to a second end of the main bore of the tee fitting, the 22 gauge needle receiving compressed air from the secondary bore and the main bore of the tee fitting;

wherein the 32 gauge tube extends through the tee fitting and the 22 gauge needle so that a second end of the 32 gauge tube extends slightly beyond the 22 gauge needle and fluid is injected from the end of the 32 gauge tube into the compressed gas flow from the annular opening between the 32 gauge tube and the 22 gauge needle In another embodiment, a system for performing inhalation research includes at atomizing system for generating an aerosol and equipment for performing tests on the aerosol, both inside a glove box containment system

DESCRIPTION OF THE DRAWINGS

Features of example implementations of the invention will become apparent from the description, the claims, and the accompanying drawings in which:

FIG. 1 is a diagram of an experimental apparatus used with an atomizing system in one embodiment of the invention.

DETAILED DESCRIPTION

Figure 1:
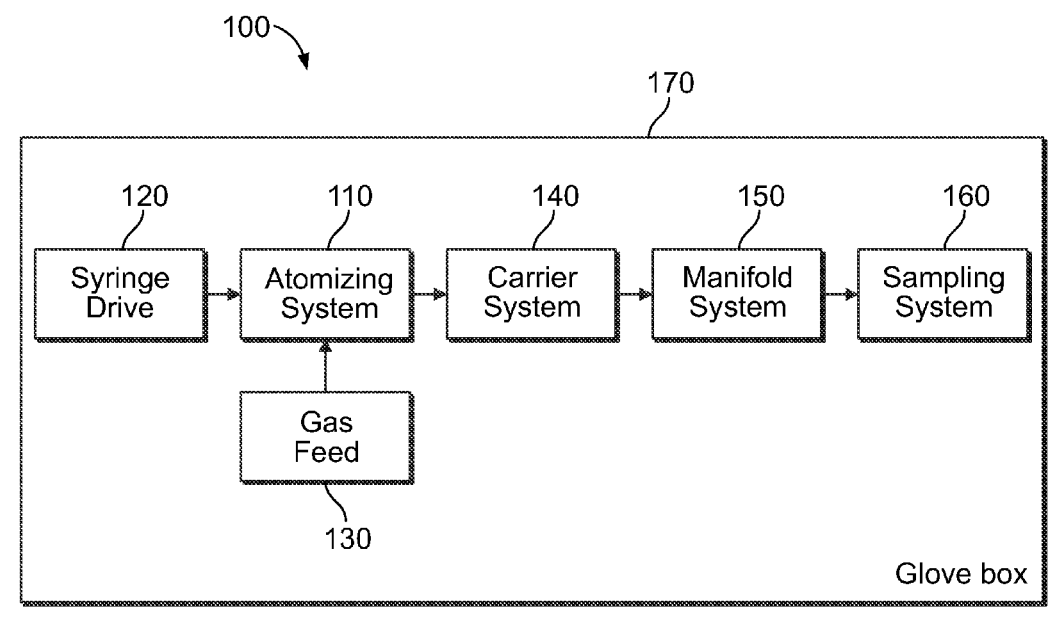
Figure 2:
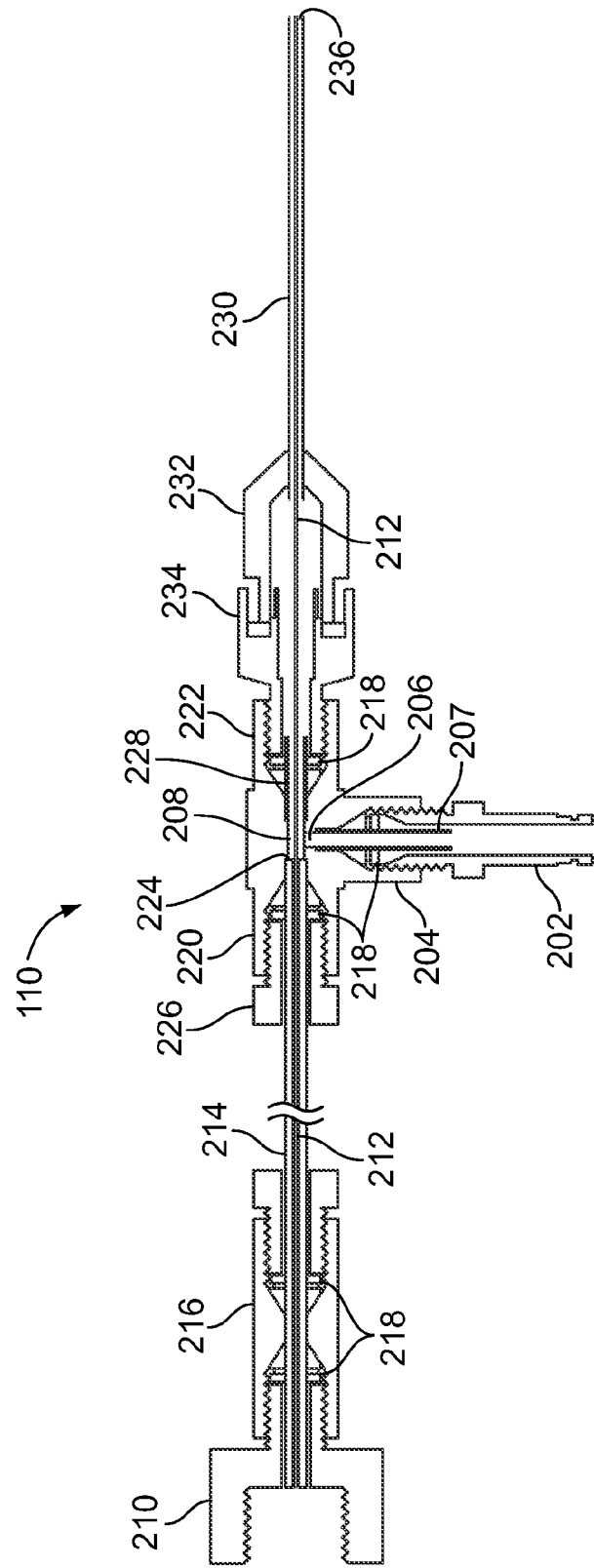
FIG. 2 is a cross-sectional view of an embodiment of the atomizing system.

Turning to FIG. 1. an apparatus 100 in one example comprises the atomizing system 110 of the present invention. Atomizing system 110 receives a continuous flow of a compound, or agent, to be atomized from syringe drive 120, for example, a Harvard Apparatus Model 22 Syringe Pump. Atomizing system 110 also receives pressurized gas from gas feed 130.

An aerosol generated by atomizing system 110 enters carrier system 140, for example, ½" stainless steel tubing. This system may optionally include other components that further modify properties of the aerosol generated by the atomizing system, for example, a spraying cylinder, a drying cylinder, a bleed off valve, a cyclone and additional air inputs.

From carrier system 140, the aerosol enters manifold system 150. Air inlets (not shown) ensure that the aerosol is evenly distributed. Finally, sampling system 160 contains equipment used in testing the aerosol, for example, aerosol monitors, particle counters, filters, cascade impactors, etc.

To accomplish inhalation research on highly toxic compounds in a safe manner, the aerosol must he double contained. Each of the systems of FIG. 1 is a closed system, and then the entire apparatus is enclosed within a glove box 170. The exhaust from apparatus is captured and processed through carbon filters or other purifying devices as well.

The use of a double containment system including glove box 170 for experiments in inhalation research imposes size constraints on systems 110-160. For example, small volume chambers are required and therefore, a low gas flow generator, for example, 1.4-2.4 l/min, is needed. It is also paramount to use neat compounds to generate the aerosol to eliminate an effects caused by solvents. Because of the toxicity and cost associated with certain compounds, it is also beneficial to use the smallest volume of agent needed to conduct an experiment.

In one embodiment of the present invention, an atomizing system which meets the requirements of both low quantities of compound and low gas flow is shown in more detail in FIG. 2. In this atomizing system, dead space is virtually non-existent at approximately 2.8 μl/foot of liquid feed line which dispenses directly into the gas stream for atomization. With no need for passivation and the ability to control feed rates, the inventive atomizing system is reliable, efficient and effective. The gas reaches critical velocity at the point of generation at less than 2 l/min. With a gas flow this low, the atomizing system can be used with a very small chamber and still produce a reliable aerosol for inhalation research.

As shown in FIG. 2, atomizing system 110 is connected to a source of compressed gas by fitting 202. The compressed gas may be of any composition. In a preferred embodiment, a high efficiency particulate air (HEPA) filter will be used in line. This HEPA filter will reduce the likelihood of clogging in the annular opening between tubing 212 and needle 230. The pressure (30-60 psi) or flow (≈1.4-2.4 l/min) is controlled with a regulator or mass flow controller respectively. In a preferred embodiment, fitting 202 would be a 1/16" Swagelok reducer but any suitable fitting may be used. The compressed gas enters a tee fitting 204, for example, a 1/16" Swagelok chromatograph union tee. Tee fitting 204 has perpendicular bores 206 and 208. A short length of stainless steel tubing 207 is used to provide a surface for ferrule 218 to tighten against so that air flow in through-bore 206 may be maintained. In a preferred embodiment, these bores are 0.05" diameter.

A removable needle (RN) type syringe, containing as fluid compound to be atomized, is coupled to the atomizing system by adapter 210, subject of a co-pending application. The syringe, for example, a Hamilton 1700 series gas tight RN syringe, is loaded with a desired compound and placed in a syringe drive, for example, Harvard Apparatus model 22 syringe pump, and connected to adapter 210. The syringe diameter is entered into the syringe drive and feed rate is set to a value in the range of approximately 0.2 μl/min to 20 μl/min in to preferred embodiment.

To provide very low dead space in the system and therefore use small amounts of compound, fluid from the syringe is transferred down the length of the atomizing system to the point of atomization by tubing 212 having a very small diameter, for example, 32 gauge stainless steel hypodermic tubing. To fortify and seal tubing 212, it is sheathed in polytetrafluoroethylene (PTFE) tubing 214. In a preferred embodiment, tubing 214 has an outer diameter of 0.0625" and an inner diameter of 0.01".

Adapter 210 is securely attached to tubing 212 sheathed in tubing 214 by means of a union fitting 216, for example, a 1/16" Swagelok chromatograph union. To provide sufficient diameter for tubing 212 and 214, union fitting 216 is bored out to 0.07". Ferrules 218 within union fitting 216 create to tight seal between tithing 212, tubing 214 and union fitting 216 and hold all components securely in place.

Tee fitting 204 has a proximal end 220 and a distal end 222. Within proximal end 220, a proximal shoulder 224 provides a stop for PTFE tubing 214 while 32 gauge tubing 212 passes through tee fitting 204. FIFE tubing also prevents air from bore 208 from leaking back towards adapter 210. End fitting 226 is used in conjunction with a ferrule 218 to securely attach the proximal end 220 to tubing 212 and 214.

In distal end 222 of tee fitting 204, a short length of stainless steel tubing 228 is used to provide a surface for ferrule 218 to tighten against so that air flow in through-bore 208 may be maintained.

A stainless steel needle 230 having a blunt tip and a base 232 is attached to the distal end 222 of tee fitting 204 by means of a liter lock titling 234. In a preferred embodiment, luer lock fitting 234 is a Popper & Sons stainless steel male liter lock to 10-32 standard thread. The threaded end of luer lock fitting 234 engages ferrule 218 to provide a secure connection to stainless steel tubing section 228.

The 32 gauge stainless steel tubing 212 extends coaxially through bore 208, liter lock fitting 234 and needle 230, To prevent sputtering at the tip, tubing 212 extends beyond needle 230 by approximately 0.03125".

An illustrative description of operation of the atomizing system 110 is presented, for explanatory purposes. Compressed gas is attached to 202 and the pressure or flow for a given experiment is set using a regulator or mass flow controller. The compressed gas travels through fitting 202, tee fitting 204, luer lock fitting 234 and needle 230 to exit the atomizing system at 236. A syringe (nut shown) is loaded with at fluid component to be tested then attached to atomizing system 110 via adapter 210. The syringe is then placed into a syringe drive. The syringe drive's diameter and feed rate are set and the syringe drive is turned on, thereby forcing the fluid in the syringe through adapter 210 and tubing 212. When the fluid reaches the end of tubing 212, it is injected into the gas flow from the annular opening 236 and the liquid is atomized.

Numerous alternative implementations of the present invention exist. For example, different sized fittings could be used as long as they are adapted to securely hold a 32 gauge needle for transferring liquid from the syringe to the end of the atomizing system.

The steps or operations described herein are just for example. There may he many variations to these steps or operations without departing from the spirit of the invention. For instance, the steps may be performed in a differing order, or steps may be added, deleted, or modified.

Although example implementations of the invention have been depicted and described in detail herein, it will be apparent to those skilled in the relevant art that various modifications, additions, substitutions, and the like can he made without departing from the spirit of the invention and these are therefore considered to be within the scope of the invention as defined in the following claims.

What is claimed is:

1. A system for performing inhalation research with aerosols, comprising:
   a containment system further comprising a glove box;
   an atomizing system for generating an aerosol, the atomizing system further comprising:
      a tee fitting haying a main bore and a secondary bore perpendicular to the main bore, the secondary bore coupled to a compressed gas source at a pressure of approximately 30-60 psi;
      a tube extending through the main bore of the tee fitting, wherein a first end of the tube adjacent to a first end of the main bore of the tee fitting is attached to a syringe and is capable of receiving a fluid compound from the syringe at a fee rate of 0.2-20 μl/min; and
      a needle attached to a second end of the main bore of the tee fitting, the needle receiving compressed gas from the secondary bore and the main bore of the tee fitting;
      wherein the tube extends through the tee fitting and the needle so that a second end of the tube extends slightly beyond the needle and fluid is injected from the end of the tube into the compressed gas flow from the annular opening between the tube and the needle; and
equipment for performing tests on the aerosol;
wherein the atomizing system and the equipment for performing tests are contained within the glove box.

2. The system of claim 1, wherein the tube is a 32 gauge stainless steel tube and the needle is a 22 gauge stainless steel needle.

* * * * *